(12) United States Patent
Stanslaski et al.

(10) Patent No.: US 9,521,979 B2
(45) Date of Patent: Dec. 20, 2016

(54) CONTROL OF SPECTRAL AGRESSORS IN A PHYSIOLOGICAL SIGNAL MONITORING DEVICE

(71) Applicant: Medtronic, Inc., Minneapolis, MN (US)

(72) Inventors: Scott R. Stanslaski, Shoreview, MN (US); David L. Carlson, Fridley, MN (US); Peng Cong, Plymouth, MN (US); Timothy J. Denison, Minneapolis, MN (US); David E. Linde, Corcoran, MN (US); Randy M. Jensen, Hampton, MN (US)

(73) Assignee: Medtronic, Inc., Minneapolis, MN (US)

( * ) Notice: Subject to any disclaimer, the term of this patent is extended or adjusted under 35 U.S.C. 154(b) by 787 days.

(21) Appl. No.: 13/862,238

(22) Filed: Apr. 12, 2013

(65) Prior Publication Data

US 2014/0276186 A1    Sep. 18, 2014

Related U.S. Application Data

(60) Provisional application No. 61/794,761, filed on Mar. 15, 2013.

(51) Int. Cl.
*A61B 5/04* (2006.01)
*H03F 1/02* (2006.01)
(Continued)

(52) U.S. Cl.
CPC ......... *A61B 5/7225* (2013.01); *A61B 5/04004* (2013.01); *A61B 5/048* (2013.01);
(Continued)

(58) Field of Classification Search
CPC . A61B 5/7225; A61B 5/0428; A61B 5/04004; A61B 5/048; A61B 5/0496; A61B 5/7217; A61N 1/3702; A61N 1/3704; A61N 1/36125; H03F 3/38; H03F 2200/261
(Continued)

(56) References Cited

U.S. PATENT DOCUMENTS 1,342,885 A    6/1920    Armstrong
3,130,373 A    4/1964    Braymer
(Continued)

FOREIGN PATENT DOCUMENTS

EP    0354060 A2    2/1990
EP    789449 A2    8/1997
(Continued)

OTHER PUBLICATIONS

Rudell et al., "Recent developments in high integration multi standard CMOS transceivers for personal communication systems," Proceedings. 1998 International Symposium on Low Power Electronics and Design, The Association for Computing Machinery, Inc. (ACM), 1998, pp. 149-154, 6 pp.
(Continued)

*Primary Examiner* — Tiffany Weston
(74) *Attorney, Agent, or Firm* — Shumaker & Sieffert, P.A.

(57) ABSTRACT

This disclosure describes techniques for controlling spectral aggressors in a sensing device that uses a chopper amplifier to amplify an input signal prior to sampling the signal. In some examples, the techniques for controlling spectral aggressors may include generating a chopper-stabilized amplified version of an input signal based on a chopper frequency, sampling the chopper-stabilized amplified version of the input signal at a sampling rate to generate a sampled signal, and analyzing a target frequency band of the sampled signal. The chopper frequency and the sampling rate may cause spectral interference that is generated due to
(Continued)

the chopper frequency to occur in the sampled signal at one or more frequencies that are outside of the target frequency band of the sampled signal. The techniques for controlling spectral aggressors may reduce the noise caused by the chopper frequency in the resulting sampled signal, thereby improving the quality of the signal.

34 Claims, 7 Drawing Sheets

(51) Int. Cl.
| | |
|---|---|
| A61B 5/00 | (2006.01) |
| A61B 5/048 | (2006.01) |
| A61N 1/36 | (2006.01) |
| A61N 1/37 | (2006.01) |
| H03F 3/38 | (2006.01) |
| A61B 5/0428 | (2006.01) |
| A61B 5/0496 | (2006.01) |

(52) U.S. Cl.
CPC ........ *A61B 5/04012* (2013.01); *A61B 5/0428* (2013.01); *A61B 5/7217* (2013.01); *A61N 1/36125* (2013.01); *A61N 1/3702* (2013.01); *A61N 1/3704* (2013.01); *H03F 3/38* (2013.01); *A61B 5/0496* (2013.01); *H03F 2200/261* (2013.01)

(58) Field of Classification Search
USPC .......................................................... 330/9
See application file for complete search history.

(56) References Cited

U.S. PATENT DOCUMENTS

| | | |
|---|---|---|
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobl et al. |
| 4,610,259 A | 9/1986 | Cohen et al. |
| 4,810,960 A | 3/1989 | Owen et al. |
| 4,933,642 A | 6/1990 | Lee |
| 4,979,230 A | 12/1990 | Marz |
| 5,061,593 A | 10/1991 | Yoerger et al. |
| 5,113,143 A | 5/1992 | Wei |
| 5,179,947 A | 1/1993 | Meyerson et al. |
| 5,206,602 A | 4/1993 | Baumgartner et al. |
| 5,311,876 A | 5/1994 | Olsen et al. |
| 5,458,117 A | 10/1995 | Chamoun et al. |
| 5,477,481 A | 12/1995 | Kerth |
| 5,619,536 A | 4/1997 | Gourgue |
| 5,663,680 A | 9/1997 | Nordeng |
| 5,725,558 A | 3/1998 | Warnke |
| 5,928,272 A | 7/1999 | Adkins et al. |
| 6,011,990 A | 1/2000 | Schultz et al. |
| 6,018,682 A | 1/2000 | Rise |
| 6,061,593 A | 5/2000 | Fischell et al. |
| 6,064,257 A | 5/2000 | Sauer |
| 6,129,681 A | 10/2000 | Kuroda et al. |
| 6,130,578 A | 10/2000 | Tang |
| 6,262,626 B1 | 7/2001 | Bakker et al. |
| 6,360,123 B1 | 3/2002 | Kimchi et al. |
| 6,456,159 B1 | 9/2002 | Brewer |
| 6,483,355 B1 | 11/2002 | Lee et al. |
| 6,584,351 B1 | 6/2003 | Ekwall |
| 6,617,838 B1 | 9/2003 | Miranda et al. |
| 6,625,436 B1 | 9/2003 | Tolson et al. |
| 6,667,760 B1 | 12/2003 | Limberg |
| 6,810,285 B2 | 10/2004 | Pless et al. |
| 6,876,842 B2 | 4/2005 | Davie |
| 6,993,380 B1 | 1/2006 | Modarres |
| 7,006,872 B2 | 2/2006 | Gielen et al. |
| 7,098,823 B2 | 8/2006 | O'Dowd et al. |
| 7,146,218 B2 | 12/2006 | Esteller et al. |
| 7,177,609 B1 | 2/2007 | Wong |
| 7,216,001 B2 | 5/2007 | Hacker et al. |
| 7,233,198 B2 | 6/2007 | Niederkorn |
| 7,385,443 B1 | 6/2008 | Denison |
| 7,391,257 B1 | 6/2008 | Denison et al. |
| 7,395,098 B2 | 7/2008 | Darabi |
| 7,622,988 B2 | 11/2009 | Denison et al. |
| 7,714,757 B2* | 5/2010 | Denison ............ A61B 5/04012 341/143 |
| 7,847,628 B2 | 12/2010 | Denison |
| 8,099,073 B1 | 1/2012 | Muller et al. |
| 8,265,769 B2 | 9/2012 | Denison |
| 8,354,881 B2 | 1/2013 | Denison |
| 2003/0146786 A1 | 8/2003 | Gulati et al. |
| 2004/0002635 A1 | 1/2004 | Hargrove et al. |
| 2004/0077967 A1 | 4/2004 | Jordan |
| 2004/0141558 A1 | 7/2004 | Plisch et al. |
| 2004/0158119 A1 | 8/2004 | Osorio et al. |
| 2004/0167418 A1 | 8/2004 | Nguyen et al. |
| 2005/0081847 A1 | 4/2005 | Lee et al. |
| 2005/0118968 A1 | 6/2005 | Cowley |
| 2005/0226356 A1 | 10/2005 | Pirzada et al. |
| 2005/0282517 A1 | 12/2005 | Cowley |
| 2006/0055456 A1 | 3/2006 | Niederkorn |
| 2006/0133550 A1 | 6/2006 | Bolton et al. |
| 2006/0135877 A1 | 6/2006 | Giftakis et al. |
| 2006/0139192 A1 | 6/2006 | Morrow et al. |
| 2006/0139193 A1 | 6/2006 | Morrow et al. |
| 2006/0173501 A1 | 8/2006 | Stickney et al. |
| 2006/0281427 A1 | 12/2006 | Isaac et al. |
| 2006/0293720 A1 | 12/2006 | DiLorenzo |
| 2007/0010755 A1 | 1/2007 | Sarkela et al. |
| 2007/0032737 A1 | 2/2007 | Causevic et al. |
| 2007/0077907 A1 | 4/2007 | Rector |
| 2007/0249953 A1 | 10/2007 | Frei et al. |
| 2009/0082691 A1* | 3/2009 | Denison ............ A61B 5/04004 600/544 |
| 2010/0327887 A1* | 12/2010 | Denison ............ A61B 5/0002 324/692 |

FOREIGN PATENT DOCUMENTS

| | | |
|---|---|---|
| GB | 1249395 | 10/1971 |
| WO | WO 02/01711 | 1/2002 |
| WO | WO 02/03087 | 1/2002 |
| WO | WO 2006/066098 A1 | 6/2006 |

OTHER PUBLICATIONS

"Baseband" entry, Academic Press Dictionary of Science and Technology, Oxford: Elsevier Science and Technology, 1992, 2 pp.
"Baseband" entry and p. 86, Authoritative Dictionary of IEEE Standard Terms (Seventh Edition), New York: IEEE, 2000, 3 pp.
Abidi, "CMOS Wireless Transceivers: the new wave," IEEE Communications Magazine, Aug. 1999, pp. 119-124.
Anderson et al., "Recording Advances for Neural Prosthetics," in Engineering in Medicine and Biology Society, Sep. 2004, 26th Annual International Conference of the IEEE, pp. 5352-5355, vol. 7.
Anderson et al., "Selecting the signals for a brain-machine interface," Curr Opin Neurobiol, vol. 14, pp. 720-726, Dec. 2004.
Bakker et al., "A CMOS Nested-Chopper Instrumentation Amplifier with 100-nV Offset," IEEE Journal of Solid-State Circuits, vol. 35, No. 12, pp. 1877-1883, Dec. 2000.
Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pp.
Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006, 2 pp.

(56) References Cited

OTHER PUBLICATIONS

Denison et al., "A 2.21µW 94nV/√Hz, Chopper-Stabilized Instrumentation Amplifier for EEG Detection in Chronic Implants" JSSC, vol. 42, No. 12, pp. 2934-2945, Dec. 2007.
Denison et al., "A 2µW 100 nV/rtHz Chopper-Stabilized Instrumentation Amplifier for Chronic Measurement of Neural Field Potentials," Solid-state circuits, IEEE Journal, vol. 42, pp. 2934-2945, Dec. 2007.
Denison et al., "An 8µW heterodyning chopper amplifier for direct extraction of 20µVrms Neuronal Brain Biomarkers," ISSCC, Jul. 2008, paper 8.1, 3 pp.
Enz et al., "Circuit Techniques for Reducing the Effects of Op-Amp Imperfections: Autozeroing, Correlated Double Sampling, and Chopper Stabilization," Proc. Of the IEEE, vol. 84, No. 11, pp. 1584-1614, Nov. 1996.
Haddad et al., "An ultra low-power dynamic translinear cardiac sense amplifier for pacemakers," Circuits and Systems, Mar. 2003, pp. V-37-V40, vol. 5.
Haddad et al., "Analog wavelet transform employing dynamic translinear circuits for cardiac signal characterization," Circuits and Systems, 2003, pp. 1-121-1-124, vol. 1.
Hadiashar et al., "A Chopper Stabilized CMOS Analog Multiplier with Ultra Low DC Offsets," Solid-State Circuits Conference, pp. 364-367, Sep. 2006.
Harrison et al., "A Low-Power Low-Noise CMOS Amplifier for Neural Recording Applications," IEEE J. of Solid-State Circuits, vol. 38, No. 6, pp. 958-965, Jun. 2003.
Harrison et al., "Local Field Potential Measurement with Low-Power Analog Integrated Circuit," Sep. 1-5, 2004, 4 pp.
Harrison et al., A Low-Power Integrated Circuit for a Wireless 100—Electrode Neural Recording System, Solid state circuits. IEEE Journal of, vol. 42, pp. 123-133, Jan. 2007.
Krusienski et al.,"A µ-Rhythm Matched Filter for Continuous Control of a Brain-Computer Interface," Biomedical Engineering, IEEE Transactions on, vol. 54, pp. 273-280, Feb. 2007.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, pp. 76-77, Mar. 2008.
Makinwa et al., A CMOS Temperature-to-frequency converter with an Inaccuracy of less than ±0.5° C. (3o) from -40° C. to 105° C., IEEE Journal of Solid State Circuits, vol. 41, No. 12 , pp. 2992-2997, Dec. 2006.
Makinwa, "Dynamic Offset Cancellation Techniques," Smart Sensor Systems '02, May 2002, 42 pp.
Martins et al., "A CMOS IC for Portable EEG Acquisition Systems," IEEE Transactions on Instrumentation and Measurement, vol. 47, No. 5, pp. 1191-1196, Oct. 1998.
Ng et al., "A CMOS Analog Front-End IC for Portable EEG/ECG Monitoring Applications," IEEE Trans. On Circuits and Systems, vol. 52 No. 11, Nov. 2005, 13 pp.
Rauscher, "Practical Realization of an Analyzer Operating on the Heterodyne Principle," part of Chapter 4 of Fundamentals of Spectrum Analysis (Rohe & Schwarz), 2001, 35 pp.
Salthouse et al., "A practical micropower programmable bandpass filter for use in bionic ears," Solid-state Circuits, IEEE Journal, vol. 38, pp. 63-70, Jan. 2003.
Sanduleanu et al., "A Low Noise, Low Residual Offset, Chopped Amplifier for Mixed Level Applications," IEEE, pp. 333-336, Sep. 1998.
Sarpeshkar et al., "An ultra-low-power programmable analog bionic ear processor," Biomedical Engineering, IEEE Transactions, vol. 52, pp. 711-727, Apr. 2005.
Sarpeshkar et al., Low power circuits for brain-machine interfaces, Circuits and Systems, Sep. 2007, pp. 2068-2071.
Sarpeshkar, "Borrowing from biology makes for low-power computing," IEEE Spectrum, pp. 24-29, May 2006.
Smart et al., "Automatic Detection of High Frequency Epileptiform Oscillations from Intracranial EEG Recordings of Patients with Neocortical Epilepsy," in Technical, Professional and Student Development Workshop, 2005 IEEE Region 5 and IEEE Denver Section, Apr. 2005, pp. 53-58.
Wattanapanitch et al., "An energy-efficient micropower neural recording amplifier," Biomedical Circuits and Systems, IEEE Transactions, vol. 1, No. 2, pp. 136-147, Jun. 2007.
Wu et al., "A 1V 2.3µW Biomedical Signal Acquisition IC," ISSCC Digest of Technical Papers 2006, paper 2.7, Feb. 2006, 2 pp.
Yates et al., "An Ultra Low Power Noise Chopper Amplifier for Wireless EEG," 49th IEEE International Midwest Symposium on Circuits and Systems, 2006, vol. 2, pp. 449-452.
Yazicioglu et al., "A 200µW Eight-Channel Acquisition ASIC for Ambulatory EEG Systems," Solid-state circuits conference, Jul. 2008, 3 pp.
Yazicioglu et al., "A 60µW 60nV/√Hz Readout Front-End for Portable Biopotential Acquisition Systems," ISSCC Digest of Technical Papers 2006, paper 2.6, Feb. 2006, 2 pp.
Ying, "Chopper Stabilized Amplifiers," Term Paper, Department of Electrical and Computer Engineering, University of Toronto, 17 pp., Nov. 12, 2001.
U.S. Appl. No. 13/862,227, by David L. Carlson, filed Apr. 12, 2013.
Nielson et al., "A CMOS Low-Noise Instrumentation Amplifier Using Chopper Modulation," Analog Integrated Circuits and Signal Processing, vol. 42(1), Jan. 2005, pp. 65-76.
International Search Report and Written Opinion of International Counterpart Application No. PCT/US2014/021708, dated Jun. 2, 2014, 10 pp.

* cited by examiner

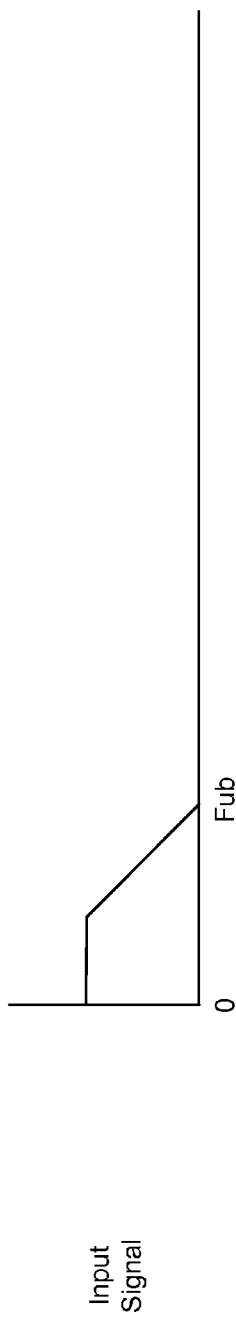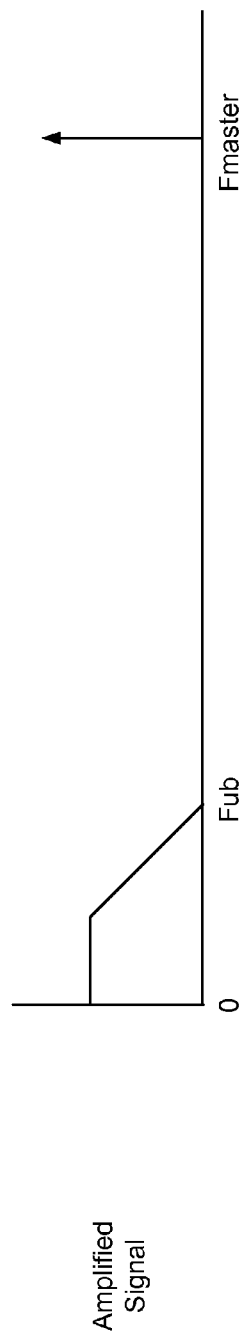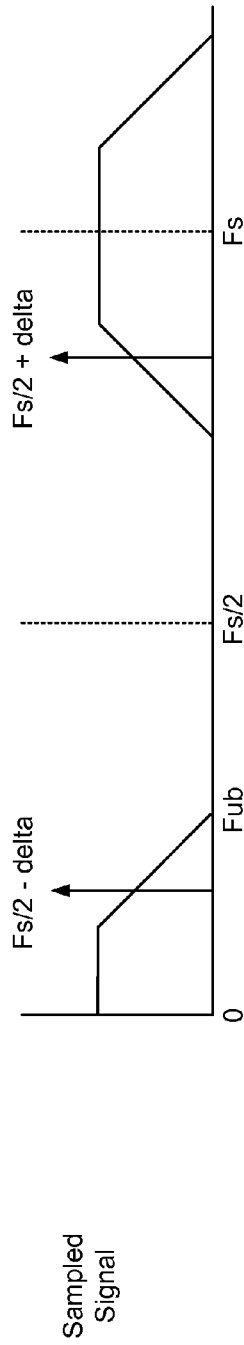

CONTROL OF SPECTRAL AGRESSORS IN A PHYSIOLOGICAL SIGNAL MONITORING DEVICE

This application claims the benefit of U.S. Provisional Application No. 61/794,761, filed Mar. 15, 2013, the entire content of which is incorporated herein by reference.

TECHNICAL FIELD

This disclosure relates to medical devices and, more particularly, to the monitoring of physiological signals with a medical device.

BACKGROUND

Medical devices may be used to deliver therapy to patients to treat a variety of symptoms or conditions. Examples of therapy include electrical stimulation therapy and drug delivery therapy. Examples of symptoms or conditions include chronic pain, tremor, akinesia, Parkinson's disease, epilepsy, dystonia, neuralgia, obsessive compulsive disorder (OCD), depression, sleep dysfunction, urinary or fecal incontinence, sexual dysfunction, obesity, or gastroparesis. Information relating to symptoms or conditions may be sensed by monitoring physiological signals, such as, e.g., electrocardiogram (ECG) signals, electromyogram (EMG) signals, electroencephalogram (EEG) signals, electrocorticogram (ECoG) signals, pressure signals, temperature signals, impedance signals, motion signals, and other types of signals. In some cases, the physiological signals associated with a patient may be relatively low voltage signals that have information encoded at relatively low frequencies in the signal, such as, e.g., brain signals. Amplifying low frequency signals may present significant challenges in medical devices, particularly in the case of implantable medical devices where power resources may be limited.

SUMMARY

This disclosure describes techniques for controlling spectral aggressors in a sensing device that uses a chopper amplifier to amplify an input signal prior to sampling the signal. In some examples, the techniques for controlling spectral aggressors may include selecting one or more of a chopper frequency for a chopper amplifier and a sampling rate for an analog-to-digital converter (ADC) such that spectral aggressors that are generated due to the chopper frequency occur at one or more frequencies that are outside of a target frequency band of interest in the sampled signal. Moving spectral aggressors that are caused by the chopper frequency to portions of the sampled signal that are outside of the target frequency band of interest may reduce the amount of noise in the target frequency band of the sampled signal, thereby improving the ability of a signal monitoring device to analyze one or more characteristics of the target frequency band.

In one example, this disclosure describes a signal monitoring device that includes a chopper amplifier configured to receive an input signal and generate a chopper-stabilized amplified version of the input signal based on a chopper frequency. The device further includes an analog-to-digital converter configured to sample the chopper-stabilized amplified version of the input signal at a sampling rate to generate a sampled signal. The device further includes a processor configured to analyze a target frequency band of the sampled signal. The chopper frequency and the sampling rate cause spectral interference that is generated by the chopper frequency to occur in the sampled signal at one or more frequencies that are outside of the target frequency band of the sampled signal.

In another example, this disclosure describes a method for monitoring a signal. The method includes generating a chopper-stabilized amplified version of an input signal based on a chopper frequency. The method further includes sampling the chopper-stabilized amplified version of the input signal at a sampling rate to generate a sampled signal. The method further includes analyzing information contained in a target frequency band of the sampled signal. The chopper frequency and the sampling rate cause spectral interference that is generated due to the chopper frequency to occur in the sampled signal at a frequency that is outside of the target frequency band of the sampled signal.

In another example, this disclosure describes an apparatus for monitoring a signal. The apparatus includes means for generating a chopper-stabilized amplified version of an input signal based on a chopper frequency. The apparatus further includes means for sampling the chopper-stabilized amplified version of the input signal at a sampling rate to generate a sampled signal. The apparatus further includes means for analyzing information contained in a target frequency band of the sampled signal. The chopper frequency and the sampling rate cause spectral interference that is generated due to the chopper frequency to occur in the sampled signal at a frequency that is outside of the target frequency band of the sampled signal.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 3A-3C are conceptual diagrams illustrating example spectral aggressors that may occur when sampling a chopper-stabilized amplified signal.

DETAILED DESCRIPTION

Figure 1:
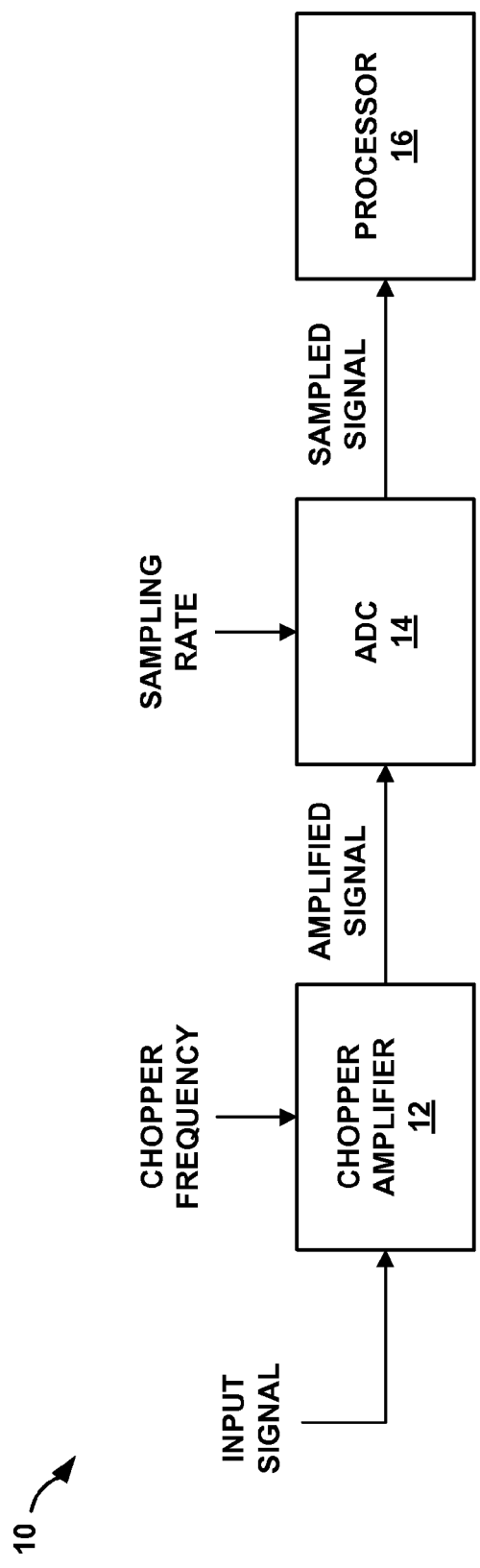
FIG. 1 is a block diagram illustrating example sensing and analysis circuitry that may be used to perform the spectral aggressor control techniques of this disclosure.

This disclosure describes techniques for controlling spectral aggressors in a sensing device that uses a chopper amplifier to amplify an input signal prior to sampling the signal. A chopper amplifier may be used to amplify a signal with low frequencies components to produce a resulting amplified signal with relatively low offset noise and relatively low 1/f noise (i.e., flicker noise or pink noise). However, the resulting amplified signal that is produced by a chopper amplifier may include a spectral aggressor (e.g., a spectral tone) at the chopper frequency due to switching effects in the amplifier. Although the spectral aggressor included in the resulting amplified signal is typically outside of a target frequency band of interest, if the amplified signal is subsequently sampled, aliasing may cause the spectral aggressor to wrap around into the target frequency band of interest in the sampled signal resulting in unwanted spectral noise.

The techniques of this disclosure may control spectral aggressors that are caused by a chopper frequency of a chopper amplifier such that the spectral aggressors occur outside of a target frequency band of interest in the sampled signal. In some examples, the spectral aggressor control techniques of this disclosure may include selecting one or more of a chopper frequency for a chopper amplifier and a sampling rate for an analog-to-digital converter (ADC) such that spectral aggressors that are generated due to the chopper frequency occur at one or more frequencies that are outside of the target frequency band of interest in the sampled signal. Moving spectral aggressors that are caused by the chopper frequency to portions of the sampled signal that are outside of the target frequency band of interest may reduce the amount of noise in the target frequency band of the sampled signal, thereby improving the ability of a signal monitoring device to analyze one or more characteristics of the target frequency band.

In some examples, the sampling rate may be selected based on a maximum frequency of the input signal. For example, the sampling rate may be selected to be greater than or equal to approximately two times the maximum frequency of the input signal. As another example, the sampling rate may be selected to be equal to approximately four times the maximum frequency of the input signal. Selecting a sampling rate that is greater than or equal to approximately two times the maximum frequency of the input signal may reduce and/or eliminate interference caused in the sampled signal due to aliasing of the frequency components in the input signal.

In further examples, the chopper frequency may be selected based on the selected sampling rate. For example, the chopper frequency may be selected to be an odd multiple of half of the sampling rate. In some cases, the odd multiple of half of the sampling rate may be selected based on noise characteristics of the amplifier included in the chopper amplifier. For example, the odd multiple of half of the sampling rate may be selected based on a 1/f corner frequency of a flicker noise characteristic of the amplifier. For instance, the odd multiple of half of the sampling rate may be selected such that the resulting chopper frequency is greater than the 1/f corner frequency of the amplifier.

Sensing circuitry designed in accordance with the techniques of this disclosure may be used for sensing, monitoring, and analyzing a variety of signals including, e.g., electrocardiogram (ECG) signals, electromyogram (EMG) signals, electroencephalogram (EEG) signals, electrocorticogram (ECoG) signals, pressure signals, temperature signals, impedance signals, motion signals, and other types of signals. In addition, sensing circuitry designed in accordance with the techniques of this disclosure may be incorporated into a variety of implantable and non-implantable medical devices including, e.g., a pacemaker, a neurological stimulator, and a deep brain stimulator.

In some examples, the techniques of this disclosure may be used to sense, monitor, and analyze brain signals, such as, e.g., EEG signals, ECoG signals, and local field potentials (LFP's). Brain signals may include neurological biomarkers that are encoded as power fluctuations in particular frequency bands of the brain signal. For example, visual processing and motor planning may be correlated with power fluctuations in the alpha band (e.g., 5 to 15 Hz), and the symptoms of Parkinson's disease may be correlated with power fluctuations in the beta band (e.g., 15 to 35 Hz). Other target frequency bands of interest for brain signal may include the delta band (e.g., 1 Hz or lower), the theta band (e.g., 4 to 8 Hz), and the gamma band (e.g., 30-100 Hz).

A digital processor may be used to analyze power fluctuations of the brain signal in a specific frequency band. The power fluctuations in the brain signal may occur at relatively low frequencies and at a relatively low baseline power. The relatively low baseline power of the brain signal may make the signal difficult to analyze in a digital processor without amplification prior to digitization. The relatively low frequencies of interest in the brain signal may make the signal difficult to amplify without introducing noise (e.g., offset noise and 1/f noise) into the target frequency bands of interest, particularly in low power applications where the available power for the amplifier may be limited.

A chopper amplifier is an example of a low power amplifier that may be used to amplify a brain signal to produce a resulting amplified signal with relatively low noise at low frequencies in the signal. A chopper amplifier may modulate a signal to be amplified based on a chopper frequency, amplify the up-modulated signal, and down-modulate the amplified signal based on the same chopper frequency to produce a chopper-stabilized amplified version of the input signal. The chopper frequency used for chopper amplification, however, may introduce a spectral aggressor into the amplified signal at the chopper frequency. For example, charge injection caused by the switches in the chopper modulators may introduce a spectral aggressor into the amplified signal at the chopper frequency. As another example, non-ideal power supply rejection and/or physical signal coupling at the integrated circuit (IC) level or device level may also introduce a spectral aggressor into the amplified signal at the chopper frequency.

The spectral aggressor introduced into the amplified signal, when sampled, may be shifted into a target frequency band of interest by the sampler. Although the chopper amplifier may include a low-pass filter, it may be difficult to design and/or implement a filter that has enough rolloff to completely eliminate a chopper frequency (i.e., $F_{master}$) aggressor in the output signal, particularly in cases where the chopper amplifier is amplifying low voltage signals (e.g., voltage signals that are on the order of 1 uV).

The techniques of this disclosure may be used to control spectral aggressors that are caused by a chopper frequency of a chopper amplifier such that the aggressors occur in portions of a sampled signal that are outside of the target frequency band of interest. Shifting the spectral aggressors outside of the target frequency band of interest in the sampled signal may reduce and/or effectively eliminate any signal degradation in the target frequency band due to such aggressors. In this way, the low power, low noise characteristics of a chopper amplifier may be leveraged while ensuring that any spectral aggressors caused by the chopper frequency of the chopper amplifier do not interfere with the target frequency band of interest that is to be analyzed in the sampled signal.

FIG. 1 is a block diagram illustrating example sensing and analysis circuitry 10 that may be used to perform the spectral aggressor control techniques of this disclosure. Sensing and analysis circuitry 10 is configured to sense and analyze an input signal received from one or more sensing elements. In some examples, the input signal may be a physiological signal received from one or more sensing elements (e.g., electrodes) that are attached to, proximate to, and/or implanted within a human being. Sensing and analysis circuitry 10 includes a chopper amplifier 12, an analog-to-digital converter (ADC) 14, and a processor 16.

Chopper amplifier 12 is configured to receive an input signal, and generate a chopper-stabilized amplified version of the input signal based on a chopper frequency. In some examples, chopper amplifier 12 may modulate an amplitude of the input signal based on a chopper frequency to produce a modulated signal, amplify an amplitude of the modulated signal to produce an amplified signal, demodulate the amplified signal to produce a demodulated signal based on the chopper frequency, and generate a chopper-stabilized amplified version of the input signal based on the demodulated signal. To generate the chopper-stabilized amplified version of the input signal based on the demodulated signal, chopper amplifier 12 may, in some examples, low-pass filter the demodulated signal.

ADC 14 is configured to receive the chopper-stabilized amplified version of the input signal from chopper amplifier 12, and sample the chopper-stabilized amplified version of the input signal at a sampling rate to generate a sampled signal. Sampling a signal may refer to the process of converting a continuous-time signal to a discrete-time signal. A sampling rate may refer to the rate or frequency at which samples of the continuous-time signal are taken. The sampling rate may alternatively be referred to as a sampling frequency. In some examples, ADC 14 may also quantize the chopper-stabilized amplified version of the input signal to produce the sampled signal. In such examples, the sampled signal may correspond to a digital signal.

Processor 16 is configured to analyze information contained in a target frequency band of the sampled signal. In some examples, processor 16 may determine a power level of the target frequency band in the sampled signal. In further examples, processor 16 may determine a power fluctuation of the target frequency band in the sampled signal. Processor 16 may be implemented as one or more digital processors, microprocessors, digital signal processors (DSPs), application specific integrated circuits (ASICs), field programmable logic arrays (FPGAs), etc.

According to this disclosure, one or more of the chopper frequency used by chopper amplifier 12 and the sampling rate used by ADC 14 may cause spectral interference that is generated due to the chopper frequency to occur in the sampled signal at one or more frequencies that are outside of the target frequency band of interest of the sampled signal. The target frequency band of interest of the sampled signal may correspond to the target frequency band of the sampled signal that is analyzed by processor 16. Causing spectral aggressors that are generated due to the chopper frequency to occur in portions of the sampled signal that are outside of the target frequency band of interest may reduce the amount of noise in the target frequency band of the sampled signal, thereby improving the ability of a signal monitoring device to analyze characteristics of the target frequency band.

In some examples, the chopper frequency of chopper amplifier 12 and the sampling rate of ADC 14 may be selected and/or configured such that spectral interference caused by the chopper frequency occurs in the sampled signal at one or more frequencies that are outside of the target frequency band of the sampled signal. For example, the sampling rate for ADC 14 may be selected based on a maximum frequency of the input signal, and the chopper frequency may be selected based on the selected sampling rate. The maximum frequency of the input signal may refer to an upper bound frequency of the input signal. In some cases, the maximum frequency of the input signal may be equal to the bandwidth of the input signal. In such cases, the sampling rate for ADC 14 may be selected based on a bandwidth of the input signal.

In some examples, the sampling rate for ADC 14 may be selected to be at least twice the maximum frequency of the input signal. Selecting a sampling rate for ADC 14 that is greater than or equal to approximately two times the maximum frequency of the input signal may reduce and/or eliminate interference caused in the sampled signal due to aliasing of the frequency components in the input signal. In further examples, the sampling rate for ADC 14 may be selected to be greater than or equal to approximately four times the maximum frequency of the input signal. In additional examples, the sampling rate for ADC 14 may be selected to be approximately equal to four times the maximum frequency of the input signal.

In further examples, the chopper frequency for chopper amplifier 12 may be selected based on the selected sampling rate for ADC 14. For example, the chopper frequency may be selected to be an odd multiple of one half of the sampling rate of ADC 14. In some cases, the particular odd multiple of one half of the sampling rate to use for the chopper frequency may be selected based on noise characteristics of the amplifier included in the chopper amplifier. For example, the particular odd multiple of one half of the sampling rate may be selected based on a 1/f corner frequency of a flicker noise characteristic of an amplifier included in chopper amplifier 12. For instance, the odd multiple of one half of the sampling rate may be selected such that the resulting chopper frequency is greater than the 1/f corner frequency of the amplifier included in chopper amplifier 12.

In additional examples, the chopper frequency for chopper amplifier 12 may be selected based on the following equation:

$$F_{master} = n * F_S + \frac{F_S}{2} \quad (1)$$

where $F_{master}$ is the chopper frequency for chopper amplifier 12, $F_S$ is the sampling rate for ADC 14, and n is a non-negative integer. In the above-recited equation, n may be used to determine which odd multiple of one half of the sampling rate is to be used for the chopper frequency.

In some examples, $F_{master}$ may be within a frequency range of approximately 2000 Hz to approximately 5000 Hz. In further examples, $F_S$ may be selected from a frequency range of approximately 200 Hz to approximately 1000 Hz. In additional examples, n may be within a range of approximately 5 to approximately 20.

In some examples, n may be selected based on a 1/f corner frequency of a flicker noise characteristic of an amplifier included in chopper amplifier 12. For instance, n may be selected such that the resulting chopper frequency is greater than the 1/f corner frequency of the amplifier included in chopper amplifier 12. In further examples, n may be equal to 10. In the above-recited equation, n may be used to determine which odd multiple of one half of the sampling rate is used for the chopper frequency.

In some examples, the chopper frequency for chopper amplifier 12 may be selected based on the sampling rate of ADC 14 and based on equation (1). In such examples, if n is selected based on a 1/f corner frequency of an amplifier included in chopper amplifier 12, then the chopper frequency for chopper amplifier 12 may be selected based on the 1/f corner frequency of the amplifier included in chopper amplifier 12, based on a sampling rate of ADC 14, and based on equation (1).

In further examples, a combination of the chopper frequency for chopper amplifier 12 and the sampling rate for ADC 14 may be selected based on equation (1) such that equation (1) is satisfied. In such examples, if n is selected based on a 1/f corner frequency of an amplifier included in chopper amplifier 12, then the combination of the chopper frequency for chopper amplifier 12 and the sampling rate for ADC 14 may be selected based on the 1/f corner frequency of the amplifier included in chopper amplifier 12 and based on equation (1) such that equation (1) is satisfied. In general, one or both of the chopper frequency for chopper amplifier 12 and the sampling rate for ADC 14 may be configured such that equation (1) is satisfied.

In yet further examples, the chopper frequency for chopper amplifier 12 may be selected based on a target spectral aggressor frequency in the sampled signal. The target spectral aggressor frequency may be a target frequency in the sampled signal for placing a spectral aggressor that is generated due to the chopper frequency of chopper amplifier 12. It should be noted that the target spectral aggressor frequency is different from, and preferably not included in, the target frequency band of interest for analysis that is performed by processor 16.

In some examples, the chopper frequency for chopper amplifier 12 may be selected based on a target spectral aggressor frequency and the following equations:

$$\delta = \frac{F_S}{2} - F_{target} \quad (2)$$

$$F_{master} = n * F_S + \frac{F_S}{2} \pm \delta \quad (3)$$

where $F_{master}$ is the chopper frequency for chopper amplifier 12, $F_{target}$ is the target spectral aggressor frequency, $F_S$ is the sampling rate for ADC 14, and n is a non-negative integer. In the above-recited equations, $\delta$ represents a difference between one half of the sampling frequency and the target spectral aggressor frequency.

In some examples, $\delta$ may be selected from a range of values between zero and one half of the sampling frequency. In further examples, $F_{master}$ may be within a frequency range of approximately 2000 Hz to approximately 5000 Hz. In additional examples, $F_S$ may be selected from a frequency range of approximately 200 Hz to approximately 1000 Hz. In yet further examples, n may be within a range of approximately 5 to approximately 20.

Similar to what was described above with respect to equation (1), n may be selected based on a 1/f corner frequency of a flicker noise characteristic of an amplifier included in chopper amplifier 12. For instance, n may be selected such that the resulting chopper frequency is greater than the 1/f corner frequency of the amplifier included in chopper amplifier 12. In the above-recited equation, n may be used to determine an odd multiple of half of the sampling rate from which $\delta$ is added or subtracted.

In some examples, the chopper frequency for chopper amplifier 12 may be selected based on the target spectral aggressor frequency, based on the sampling rate of ADC 14, and based on equations (2) and (3). In such examples, if n is selected based on a 1/f corner frequency of an amplifier included in chopper amplifier 12, then the chopper frequency for chopper amplifier 12 may be selected based on the 1/f corner frequency of the amplifier included in chopper amplifier 12, based on the target spectral aggressor frequency, based on the sampling rate of ADC 14, and based on equations (2) and (3).

In further examples, a combination of the chopper frequency and the sampling rate may be selected based on a target spectral aggressor frequency and based on equations (2) and (3) such that equations (2) and (3) are satisfied. In such examples, if n is selected based on a 1/f corner frequency of an amplifier included in chopper amplifier 12, then the chopper frequency for chopper amplifier 12 may be selected based on the 1/f corner frequency of the amplifier included in chopper amplifier 12, based on a target spectral aggressor frequency and based on equations (2) and (3) such that equations (2) and (3) are satisfied. In general, one or both of the chopper frequency for chopper amplifier 12 and the sampling rate for ADC 14 may be configured such that equations (2) and (3) are satisfied.

In some examples, the target spectral aggressor frequency may be selected to be between an upper bound frequency of the input signal and half of the sampling frequency. In further examples, the target spectral aggressor frequency may be selected to be between half of the sampling frequency and a frequency that corresponds to the sampling frequency minus the upper bound frequency of the input signal.

In additional examples, the target spectral aggressor frequency may be selected to be between a direct current frequency (i.e., 0 Hz) and a lower bound frequency of the input signal. In yet further examples, the target spectral aggressor frequency may be selected to be between the sampling frequency and a frequency that corresponds to the sampling frequency minus the lower bound frequency of the input signal.

In some examples, a delta range may be used to select one or both of a chopper frequency for chopper amplifier 12 and a sampling rate for ADC 14. The delta range may define a range of target spectral aggressor frequencies in which a spectral aggressor that is generated due to the chopper frequency may be placed. The range of target spectral aggressor frequencies may, in some examples, not include frequencies in the target frequency band of interest that is used for analysis by processor 16.

In examples where a delta range is used, one or both of a chopper frequency for chopper amplifier 12 and a sampling rate for ADC 14 may be selected based on equation (3) and the delta range such that equation (3) is satisfied. Selecting one or both of a chopper frequency for chopper amplifier 12 and a sampling rate for ADC 14 based a delta range may refer to using delta values within the delta range for the selection and not using delta values that are not within the delta range for the selection.

In some examples, the chopper frequency for chopper amplifier 12 may be selected based on the sampling rate of ADC 14, based on the delta range, and based on equation (3) such that equation (3) is satisfied. In such examples, if n is selected based on a 1/f corner frequency of an amplifier included in chopper amplifier 12, then the chopper frequency for chopper amplifier 12 may be selected based on the 1/f corner frequency of the amplifier included in chopper amplifier 12, based on the sampling rate of ADC 14, based on the delta range, and based on equation (3) such that equation (3) is satisfied.

In further examples, a combination of the chopper frequency for chopper amplifier 12 and the sampling rate for ADC 14 may be selected based on the delta range, and based on equation (3) such that equation (3) is satisfied. In such examples, if n is selected based on a 1/f corner frequency of an amplifier included in chopper amplifier 12, then the combination of the chopper frequency for chopper amplifier 12 and the sampling rate for ADC 14 may be selected based on the 1/f corner frequency of the amplifier included in chopper amplifier 12, based on the delta range, and based on equation (3) such that equation (3) is satisfied.

In some examples, the delta range may be selected based on a maximum allowable delta. In such examples, the delta range may correspond to delta values between zero and the maximum allowable delta inclusive of zero and the maximum allowable delta. In such examples, the maximum allowable delta may be selected, in some examples, based on an upper bound frequency of the input signal and based on the sampling rate of ADC 14. For example, the maximum allowable delta may be selected to be equal to one half of the sampling rate minus the upper bound frequency.

In further examples, the delta range may be selected based on a minimum allowable delta. In such examples, the delta range may correspond to delta values between the minimum allowable delta and one half of the sampling rate inclusive of the values corresponding to the minimum allowable delta and one half of the sampling rate. In such examples, the minimum allowable delta may be selected, in some examples, based on a lower bound frequency of the input signal and based on the sampling rate of ADC 14. For example, the minimum allowable delta may be selected to be equal to one half of the sampling rate minus the lower bound frequency.

In additional examples, the delta range may be selected based on a maximum allowable delta for a lower portion of a delta range and a minimum allowable delta for an upper portion of the delta range. In such examples, the delta range may correspond to the union of the lower portion and the upper portion. The lower portion of the delta range may correspond to delta values between zero and the maximum allowable delta for the lower portion of the delta range inclusive of zero and the maximum allowable delta. The upper portion of the delta range may correspond to delta values between the minimum allowable delta for the upper portion of the delta range and one half of the sampling rate inclusive of the values corresponding to the minimum allowable delta and one half of the sampling rate.

In such examples, the maximum allowable delta for the lower portion of the delta range may be selected, in some examples, based on an upper bound frequency of the input signal and based on the sampling rate of ADC 14. For example, the maximum allowable delta may be selected to be equal to one half of the sampling rate minus the upper bound frequency. The minimum allowable delta for the upper portion of the delta range may be selected, in some examples, based on a lower bound frequency of the input signal and based on the sampling rate of ADC 14. For example, the minimum allowable delta may be selected to be equal to one half of the sampling rate minus the lower bound frequency.

It should be noted that equation (1) is a special case of equation (3) where δ is set to zero. Setting δ equal to zero corresponds to selecting a target spectral aggressor frequency that is equal to one half of the sampling rate. In other words, for examples that use equation (1), the chopper frequency for chopper amplifier 12 may selected such that spectral interference caused by the chopper frequency occurs in the sampled signal at a frequency that is equal to one half of the sampling rate. Setting the target spectral aggressor frequency to one half of the sampling rate may cause a single spectral tone that is positioned at a single frequency (i.e., one half of the sampling frequency) to be generated due to the chopper frequency in contrast to choosing other target spectral aggressor frequencies that may generate two separate tones at two different frequencies (i.e., the target spectral aggressor frequency and an alias frequency corresponding to the target spectral aggressor frequency).

Figure 2:
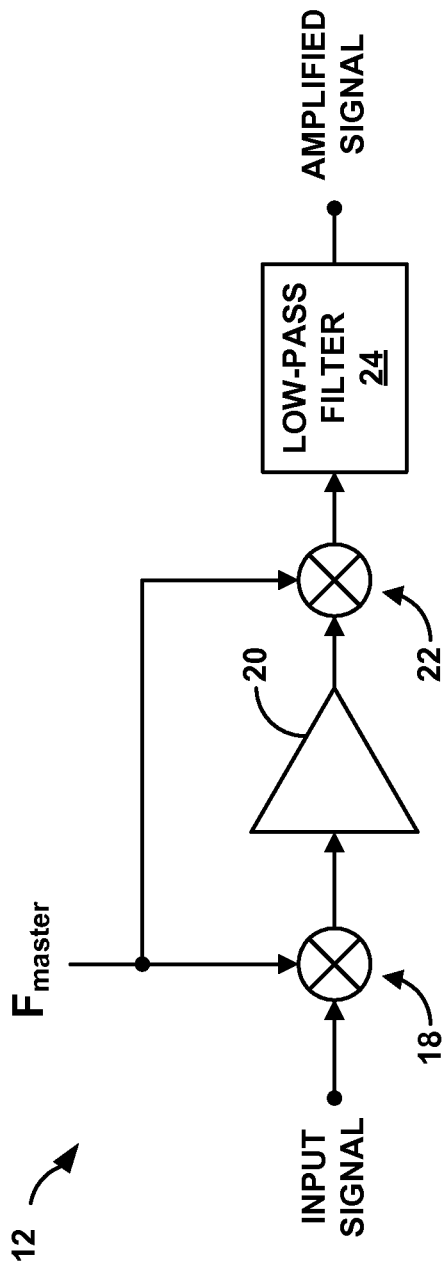
FIG. 2 is a block diagram illustrating an example chopper amplifier that may be used in the sensing circuitry of FIG. 1.

FIG. 2 is a block diagram illustrating an example chopper amplifier 12 that may be used in the sensing circuitry 10 of FIG. 1. Chopper amplifier 12 is configured to receive an input signal and generate a chopper-stabilized amplified version of the input signal based on a chopper frequency (i.e., $F_{master}$). Chopper amplifier 12 includes a modulator 18, an amplifier 20, a demodulator 22, and a low-pass filter 24.

Modulator 18 modulates an amplitude of the input signal based on the chopper frequency (i.e., $F_{master}$) to produce a modulated signal. Amplifier 20 amplifies an amplitude of the modulated signal to produce an amplified signal. Demodulator 22 demodulates the amplified signal based on the chopper frequency (i.e., $F_{master}$) to produce a demodulated signal. Low-pass filter 24 low-pass filters the demodulated signal to generate a chopper-stabilized amplified version of the input signal.

Modulating and demodulating a signal based on a chopper frequency may refer, respectively, to modulating and demodulating the signal at the chopper frequency. In other words, modulator 18 and demodulator 22 may multiply a signal received by the respective modulator with the chopper frequency to produce an output signal (e.g., a modulated signal or a demodulated signal). In some examples, demodulator 22 may also be referred to as a modulator. In some cases, modulator 18 and demodulator 22 may be constructed from one or more switches that are switched at the chopper frequency.

Amplifier 20 may be any type of amplifier with any combination of single-ended or differential inputs and outputs. If the inputs to amplifier 20 are single-ended, then amplifier 20 may amplify the single-ended input signal to generate an amplified version of the input signal. On the other hand, if the inputs to amplifier 20 are differential, then amplifier 20 may amplify a difference between the input signals to generate an amplified version of the input signal.

In some examples, amplifier 20 may produce an amplified signal that includes flicker noise (i.e., 1/f noise). The flicker noise produced by amplifier 20 may be specified by a flicker noise characteristic, which may specify a 1/f corner frequency for the flicker noise. In some examples, one or both of a chopper frequency for chopper amplifier 12 and a sampling rate for ADC 14 (FIG. 1) may be selected based on the 1/f corner frequency of the flicker noise characteristic of chopper amplifier 12 as described in this disclosure.

Low-pass filter 24 may be any type of low-pass filter including, e.g., an integrator or a type of low-pass filter that includes a pass band and a stop band. In some cases, it may be difficult to design and/or implement a low-pass filter that has enough rolloff to completely eliminate a chopper frequency (i.e., $F_{master}$) aggressor in the output signal, particularly in cases when chopper amplifier 12 is amplifying low voltage signals (e.g., voltage signals on the order of 1 uV). Although the chopper frequency aggressor included in the resulting amplified signal is typically outside of a target frequency band of interest, if the amplified signal is subsequently sampled, aliasing may cause the spectral aggressor to wrap around into the target frequency band of interest in the sampled signal resulting in an unwanted spectral noise.

The techniques of this disclosure may control the spectral aggressors that are caused by the chopper frequency of chopper amplifier 12 such that the spectral aggressors occur outside of the target frequency band of interest in the sampled signal. Moving the spectral aggressors that are caused by the chopper frequency to portions of the sampled signal that are outside of the target frequency band of interest may reduce the amount of noise in the target frequency band of the sampled signal. In other words, even though a low-pass filter may not have enough rolloff to completely eliminate a chopper frequency aggressor, the techniques of this disclosure may move the aggressor to a frequency, which when sampled, does not interfere with the analysis of the target frequency band of interest in the sampled signal.

Figure 6:
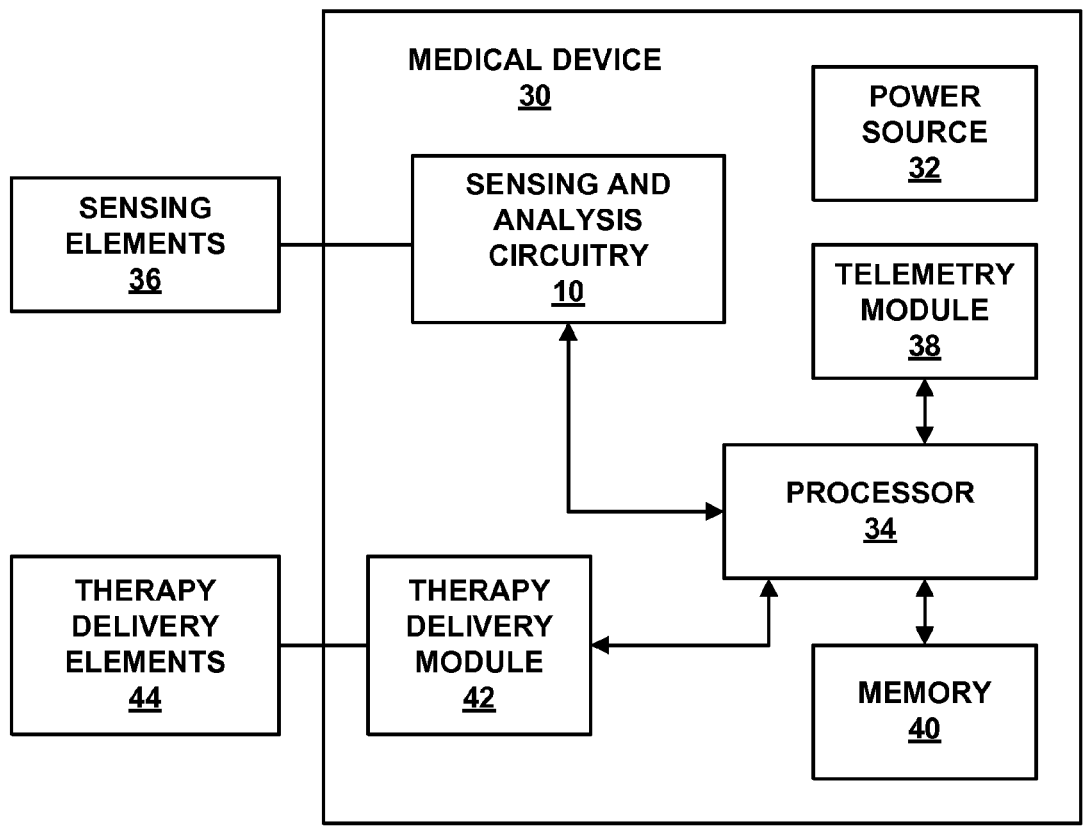
FIG. 6 is block diagram illustrating an example medical device in which the spectral aggressor control techniques of this disclosure may be implemented.

Although amplifier 20 and demodulator 22 are illustrated in FIG. 2 as being separate components, in some examples, amplifier 20 and demodulator 22 may be integrated into a single mixer amplifier component. The single mixer amplifier component may be a modified folded-cascode amplifier with switching at low impedance nodes. An example of a modified folded-cascode amplifier with switching at low impedance nodes is shown in FIG. 6 of and described in the corresponding description of U.S. Pat. No. 7,385,443, issued Jun. 10, 2008, to Timothy J. Denison, entitled "Chopper Stabilized Instrumentation Amplifier," the entire content of which is incorporated herein by reference. Other examples of modified folded-cascode amplifiers with switching at low impedance nodes are shown in FIGS. 3A and 3B of and described in the corresponding description of U.S. Pat. No. 7,714,757, issued May 11, 2010, to Timothy J. Denison et al., entitled "Chopper-stabilized analog-to-digital converter," the entire content of which is incorporated herein by reference. An additional example of a modified folded-cascode amplifier with switching at low impedance nodes is shown in FIG. 12 of and described in the corresponding description of U.S. Patent Publication No. 2009/0082691, published Mar. 26, 2009, to Timothy J. Denison et al., entitled "FREQUENCY SELECTIVE MONITORING OF PHYSIOLOGICAL SIGNALS," the entire content of which is incorporated herein by reference.

The chopper amplifier illustrated in FIG. 2 is merely one example of a chopper amplifier that may be used in accordance with the techniques of this disclosure. In further examples, chopper amplifier 12 may be a nested chopper amplifier, may include in-phase and quadrature phase signal processing pathways, or may be a nested chopper amplifier that includes in-phase and quadrature phase signal processing pathways. An example of a nested chopper amplifier that includes in-phase and quadrature phase signal processing pathways is shown in FIG. 26 of U.S. Patent Publication No. 2009/0082691, published Mar. 26, 2009, to Timothy J. Denison et al., entitled "FREQUENCY SELECTIVE MONITORING OF PHYSIOLOGICAL SIGNALS," the entire content of which is incorporated herein by reference. The nested chopper amplifier in FIG. 26 may, in some examples, have a delta set equal to zero.

FIGS. 3A-3C are conceptual diagrams illustrating example spectral aggressors that may occur when sampling a chopper-stabilized amplified signal. The diagrams illustrated in FIGS. 3A-3C are spectral diagrams where the x-axis represents frequency and the y-axis represents power.

FIG. 3A illustrates the power spectrum of an input signal that is received by chopper amplifier 12, which may correspond to an input signal received by modulator 18. As shown in FIG. 3A, the lower bound frequency of the input signal is zero Hz and the upper bound frequency of the input signal is $F_{ub}$.

FIG. 3B illustrates the power spectrum of the input signal after chopper-stabilized amplification by chopper amplifier 12. The power spectrum shown in FIG. 3B may correspond to the power spectrum of the signal received by ADC 14 in FIG. 1, the signal output by chopper amplifier 12 in FIG. 1, the signal generated by demodulator 22 in FIG. 2, or the signal generated by low-pass filter 24 in FIG. 2. As shown in FIG. 3B, the power spectrum of the amplified version of the input signal is substantially similar to the power spectrum of the input signal prior to amplification except that a spectral aggressor is present at the chopper frequency (i.e., $F_{master}$).

FIG. 3C illustrates the power spectrum of the signal after sampling by ADC 14. The power spectrum shown in FIG. 3C may correspond to the power spectrum of the signal received by processor 16 in FIG. 1 or the signal output by ADC 14 in FIG. 1. As shown in FIG. 3C, the power spectrum of the sampled version of the amplified signal is substantially similar to the power spectrum of the amplified signal except that aliasing has caused the chopper frequency spectral aggressor to wrap around into the target frequency band of interest (i.e., the frequency band of the input signal (i.e., from 0 Hz to $F_{ub}$)). Aliasing has also caused an aliased version of the input signal to appear at a frequency centered at the sampling frequency. The aliased version of the input signal also includes a chopper frequency spectral aggressor due to aliasing. These spectral aggressors, when present in the target frequency band of interest (as is shown in FIG. 3C) may interfere with the sensing and monitoring of characteristics in the target frequency band of interest.

Figure 4A:
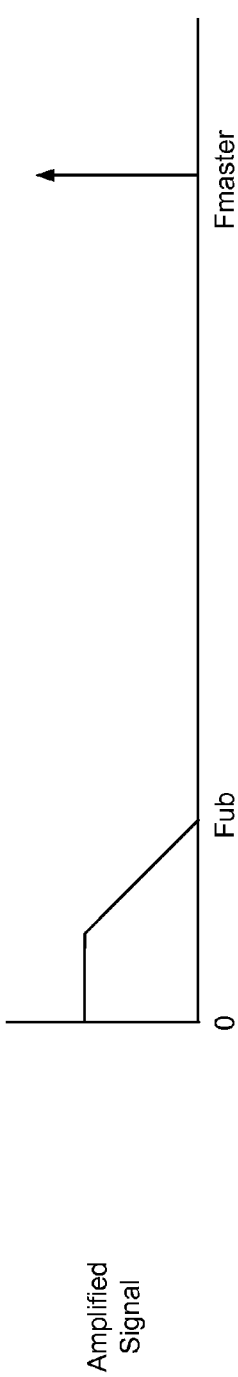
FIGS. 4A-4C are conceptual diagrams illustrating an example of how example spectral aggressor control techniques of this disclosure may be used to move spectral aggressors out of a target frequency band of interest.
Figure 4B:
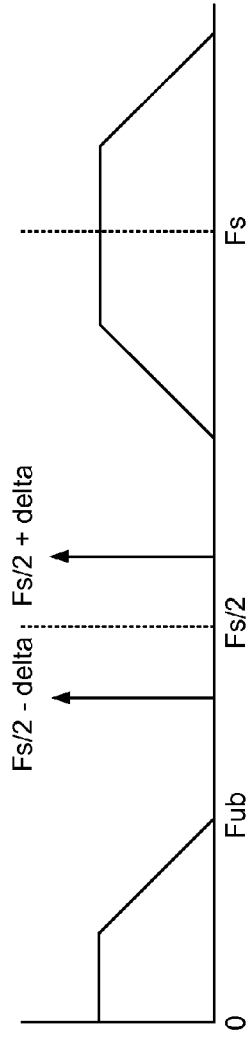
Figure 4C:
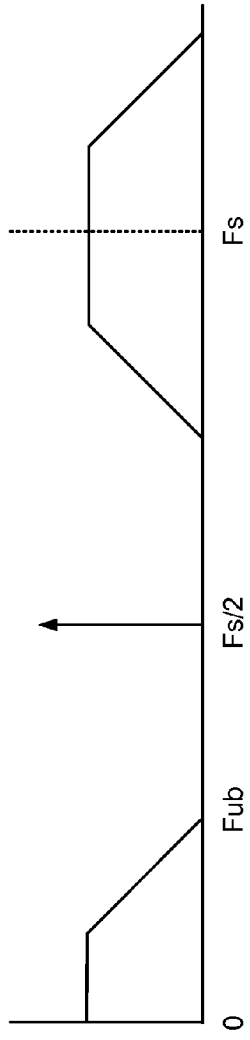

FIGS. 4A-4C are conceptual diagrams illustrating an example of how example spectral aggressor control techniques of this disclosure may be used to move the spectral aggressors out of a target frequency band of interest in the sampled signal. Similar to FIGS. 3A-3C, the diagrams illustrated in FIGS. 4A-4C are spectral diagrams where the x-axis represents frequency and the y-axis represents power.

FIG. 4A illustrates the power spectrum of the input signal after chopper-stabilized amplification by chopper amplifier 12. FIG. 4A is identical to FIG. 3B, but is reproduced here for ease of comparison with the conceptual diagrams of FIGS. 4B and 4C.

FIG. 4B illustrates an example power spectrum of the signal after sampling by ADC 14 when spectral aggressor control techniques are used according to this disclosure. The power spectrum is similar to that of FIG. 3C except that the spectral aggressors have been moved, using the spectral aggressor control techniques of this disclosure, to frequencies that are outside of the target frequency band of interest (i.e., the frequency band of the input signal, which corresponds to a frequency band defined between 0 Hz to $F_{ub}$).

Any of the techniques described in this disclosure may be used to move the spectral aggressors out of the target frequency band of interest. In some examples, a target spectral aggressor frequency may be selected to be between an upper bound frequency ($F_{ub}$) of the input signal and one half of the sampling frequency ($F_s/2$). In such examples, a chopper frequency may be selected, in some examples, based on the target spectral aggressor frequency and based on equations (2) and (3). For example, a delta may be determined based on the target spectral aggressor frequency, a sampling rate, and equation (2). In this example, the chopper frequency may be determined based on the determined delta, the sampling rate, and equation (3). In some cases, an n for equation (3) may be selected such that the resulting chopper frequency is greater than the 1/f corner frequency of the amplifier included in chopper amplifier 12.

In some examples, rather than using equation (3), the chopper frequency (i.e., $F_{master}$) in the example of FIG. 4B may be selected based on the following equation:

$$F_{master} = n * F_S + \frac{F_S}{2} + \delta \quad (4)$$

where $F_{master}$ is the chopper frequency for chopper amplifier 12, $F_{target}$ is a target spectral aggressor frequency, $F_S$ is the sampling rate for ADC 14, and n is a non-negative integer.

Moving the spectral aggressors that are caused by the chopper frequency to portions of the sampled signal that are outside of the target frequency band of interest may reduce the amount of noise in the target frequency band of the sampled signal. In this manner, a signal monitoring device may be able to monitor characteristics of the target frequency band without interference and/or with reduced interference from chopper frequency spectral aggressors.

FIG. 4C illustrates another example power spectrum of the signal after sampling by ADC 14 when spectral aggressor control techniques are used according to this disclosure. The power spectrum is similar to that of FIG. 4B except that instead of two different spectral aggressors occurring at delta offsets of one half of the sampling frequency, a single spectral aggressor occurs at one half of the sampling frequency (i.e., $F_s/2$), which is outside of the target frequency band of interest (i.e., the frequency band of the input signal, which corresponds to a frequency band defined between 0 Hz to $F_{ub}$).

Any of the techniques described in this disclosure may be used to move the spectral aggressors to one half of the sampling frequency. In some examples, the technique described with respect to FIG. 4B may be used with a target spectral aggressor frequency of one half of the sampling frequency and a corresponding delta of zero. In further examples, a chopper frequency may be selected based on the sampling rate and equation (1). In some cases, an n for equation (1) may be selected such that the resulting chopper frequency is greater than the 1/f corner frequency of the amplifier included in chopper amplifier 12.

Moving the spectral aggressor that is caused by the chopper frequency to a portion of the sampled signal that is outside of the target frequency band of interest may reduce the amount of noise in the target frequency band of the sampled signal. In this manner, a signal monitoring device may be able to monitor characteristics of the target frequency band without interference and/or with reduced interference from chopper frequency spectral aggressors.

Figure 5A:
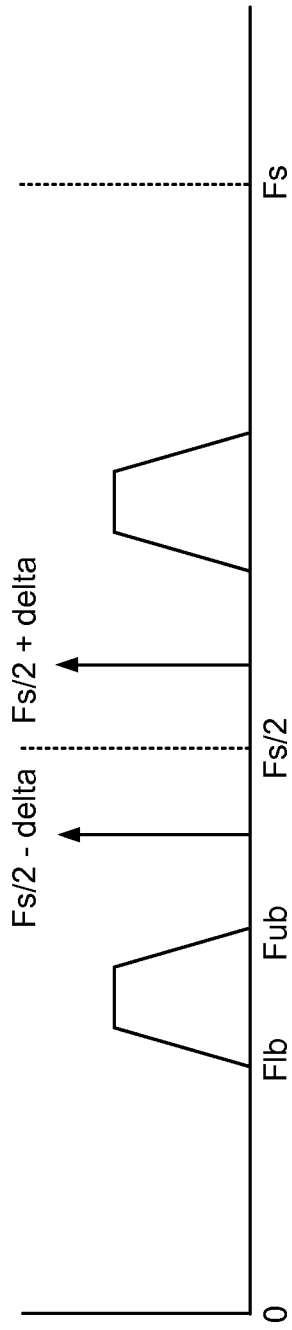
FIGS. 5A and 5B are conceptual diagrams illustrating an example of how example spectral aggressor control techniques of this disclosure may be used to move spectral aggressors out of a target frequency band of interest that is not positioned at zero Hertz.
Figure 5B:
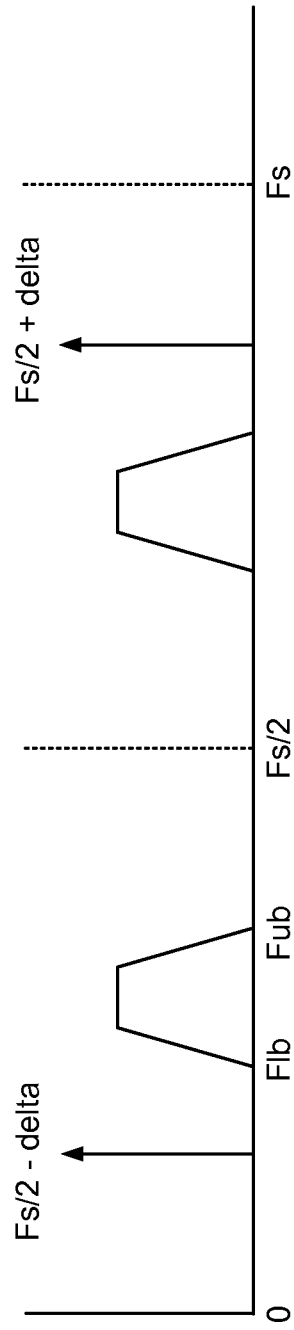

FIGS. 5A and 5B are conceptual diagrams illustrating an example of how example spectral aggressor control techniques of this disclosure may be used to move spectral aggressors out of a target frequency band of interest that is not located at zero Hz. Similar to FIGS. 3A-3C, the diagrams illustrated in FIGS. 5A and 5B are spectral diagrams where the x-axis represents frequency and the y-axis represents power. As shown in FIGS. 5A and 5B, the lower bound frequency of the input signal is $F_{lb}$ and the upper bound frequency of the input signal is $F_{ub}$.

FIG. 5A illustrates an example where the target spectral aggressor frequency is selected to be between an upper bound frequency of the input signal and one half of the sampling frequency. FIG. 5B illustrates an example where the target spectral aggressor frequency is selected to be between a direct current frequency (i.e., 0 Hz) and a lower bound frequency of the input signal.

FIG. 6 is block diagram illustrating an example medical device 30 in which the spectral aggressor control techniques of this disclosure may be implemented. Sensing and analysis circuitry 10 may monitor and/or analyze physiological signals associated with a patient in selected frequency bands. The physiological signals may be relatively low frequency signals, and may have frequency bands of interest in a range of approximately 1 to 1000 Hertz (Hz) and, more particularly, in a range of approximately 1 to 500 Hz. For example, 1 Hz oscillations may be relevant for sleep state analysis, while fast ripples in a range of approximately 200 to 500 Hz or higher may be relevant for analysis of epilepsy. In general, frequencies in the selected frequency band are less than or equal to approximately 1000 Hz, more particularly less than or equal to approximately 500 Hz, and still more particularly less than or equal to approximately 100 Hz. For EEG signals, as an example, selected frequency bands may fall in the ranges of approximately 5 to 15 Hz (alpha band), 15 to 35 Hz (beta band), and 30 to 80 Hz (gamma band). Characteristics of the signal in selected frequency bands may be useful in controlling therapy, such as electrical stimulation or drug delivery, either by initiation of delivery of therapy or adjustment of therapy parameters. Adjustment of therapy parameters may include adjustment of pulse amplitude, pulse rate, pulse width, electrode combination or the like for electrical stimulation, or adjustment of dosage, rate, frequency, lockout interval, or the like for drug delivery.

As illustrated in FIG. 6, medical device 30 may also include a power source 32, such as a rechargeable or nonrechargeable battery, a processor 34, a telemetry module 38, a memory 40, and a therapy delivery module 42. In addition, in the example of FIG. 6, sensing and analysis circuitry 10 is connected to sensing elements 36 that are positioned at a desired location relative to the patient and that detect the physiological signal. Sensing elements 36 may include a set of electrodes for sensing electrical signals. The electrodes may be, for example, implantable electrodes deployed on a lead or external surface electrodes. Sensing elements 36 may be deployed at selected tissue sites or on selected surfaces of a human patient, such as within the brain, proximate the spinal cord, on the scalp, or elsewhere. As an example, scalp electrodes may be used to measure or record EEG signals. As another example, electrodes implanted at the surface of the cortex may be used to measure or record ECoG signals. Therapy delivery module 42 may be connected to therapy delivery elements 44, such as one or more electrodes deployed on a lead or drug delivery conduits, which may be positioned at a desired location relative to the patient to deliver therapy to the patient in response to the monitored physiological signal.

In some embodiments, medical device 30 may comprise an implantable medical device capable of being implanted within the patient. In this case, sensing elements 36 may be positioned at a desired location within the patient to detect the physiological signal. Further, therapy delivery elements 44 may be positioned at a desired location within the patient to deliver the therapy, such as electrical stimulation, drug delivery or internal audio or visual cueing. In other embodiments, medical device 30 may comprise an external medical device with sensing elements positioned at a desired location adjacent the patient to detect the physiological signal. In addition, therapy delivery elements 44 may be positioned at a desired location external to the patient to deliver the therapy, such as external audio, visual or tactile cueing via lights, displays, speakers, or the like.

Processor 34, sensing and analysis circuitry 10, telemetry module 38, memory 40, and therapy delivery module 42 receive operating power from power source 32. Power source 32 may take the form of a small, rechargeable or non-rechargeable battery, or an inductive power interface that receives inductively coupled energy. In the case of a rechargeable battery, power source 32 similarly may include an inductive power interface for transfer of recharge power.

Processor 34 may include one or more microprocessors, microcontrollers, digital signal processors (DSPs), application specific integrated circuits (ASICs), field programmable gate array (FPGAs), discrete logic circuitry, or a combination of such components. In some examples, processor 34 in medical device 30 may be the same processor as processor 16 in sensing and analysis circuitry 10. In additional examples, processor in medical device 30 may be different than processor 16 in sensing and analysis circuitry 10.

Memory 40 may store therapy instructions that are available to be selected by processor 34 in response to receiving a patient therapy trigger from sensing and analysis circuitry 10. In addition, processor 34 may be configured to record diagnostic information, such as sensed signals, signal characteristics, or the like in memory 40 or another memory or storage device. Memory 40 may include any combination of volatile, non-volatile, removable, magnetic, optical, or solid state media, such as read-only memory (ROM), random access memory (RAM), electronically-erasable programmable ROM (EEPROM), flash memory, or the like.

Sensing and analysis circuitry 10 may monitor a variety of signals via a variety of different sensing elements 36, such as a pressure sensing element, an accelerometer, an activity monitor, an impedance monitor, an electrical signal monitor or other monitor configured to monitor heart sounds, brain signals, and/or other physiological signals. As an illustration, sensing elements 36 may comprise one or more electrodes located on a lead implanted at a target site within the patient and electrically coupled to sensing and analysis circuitry 10 via conductors. Sensing and analysis circuitry 10 may monitor the signals obtained from sensing elements 36. Sensing and analysis circuitry 10 may include suitable electrical interconnections to sensing elements 36 and other components, as necessary.

A lead may carry one electrode or multiple electrodes, such as ring electrodes, segmented electrodes or electrodes arranged in a planar or non-planar array, e.g., on a paddle lead. Medical device 30 may be implantable or external. Such leads may carry sense electrodes or a combination of sense and stimulation electrodes. In some cases, different leads may be dedicated to sensing and stimulation functions. If external, medical device 30 may be coupled to one or more leads carrying sense and/or stimulation electrodes via a percutaneous extension. As a further illustration, sensing elements 36 may be surface electrodes suitable for placement on scalp, face, chest, or elsewhere on a patient, in which case such electrodes may be coupled to sensing and analysis circuitry 10 via conductors within external leads. Sensing elements 36 may further comprise combinations of electrodes provided on one or more implantable leads and on or within a housing of medical device 30, or other electrode arrangements.

In general, sensing elements 36 provide a measurement of a physiological signal associated with the patient by translating the signal to an output voltage or current. Sensing and analysis circuitry 10 may receive the measured physiological signal as an input signal, generate a chopper-stabilized amplified version of the input signal based on a chopper frequency, sample the chopper-stabilized amplified version of the physiological input signal at a sampling rate to generate a sampled signal, and analyze information contained in a target frequency band of the sampled signal. The chopper frequency and the sampling rate may cause spectral interference that is generated by the chopper frequency to occur in the sampled signal at one or more frequencies that are outside of the target frequency band of the sampled signal, thereby improving the quality of the signal.

In some examples, sensing and analysis circuitry 10 may measure the power in the target frequency band or power fluctuations in the target frequency band. The measured power may be used, for example, to determine whether the delivery of therapy is triggered or initiated and/or whether the recording of diagnostic information is triggered or initiated.

In some examples, sensing and analysis circuitry 10 may generate a signal indicative of the power of a target frequency band of the physiological signal and/or a signal indicative of power fluctuation of a target frequency band of the physiological signal. In such examples, processor 34 may trigger the delivery of therapy and/or trigger the recording of diagnostic information based on the signal indicative of the power of the target frequency band and/or the signal indicative of power fluctuation of the target frequency band.

In further examples, sensing and analysis circuitry 10 may output a trigger signal to processor 34 to control therapy and/or record diagnostic information. In such examples, processor 34 may receive the trigger signal and initiate delivery of therapy or adjust one or more therapy parameters specified in memory 40.

Processor 34 may output therapy instructions to therapy delivery module 42 to initiate or adjust delivery of therapy. Therapy delivery module 42 may include a stimulation generator that delivers stimulation therapy to the patient via therapy delivery elements 44 in response to receiving the therapy instructions. Therapy delivery elements 44 may be electrodes carried on one or more leads, electrodes on the housing of medical device 30, or electrodes on both a lead and the medical device housing. Alternatively, therapy delivery module 42 may include a fluid delivery device, such as a drug delivery device, including a fluid reservoir and one or more fluid delivery conduits. For cueing applications, therapy delivery module 42 may include one or more speakers, one or more lights, one or more display screens, or any combination thereof.

In some cases, as described above, therapy delivery module 42 may include a stimulation generator or other stimulation circuitry that delivers electrical signals, e.g., pulses or substantially continuous signals, such as sinusoidal signals, to the patient via at least some of the electrodes that form therapy delivery elements 44 under the control of the therapy instructions received from processor 34. Processor 34 may control therapy delivery module 42 to deliver electrical stimulation with pulse voltage or current amplitudes, pulse widths, and frequencies (i.e., pulse rates), and electrode combinations specified by the programs of the selected therapy instructions, e.g., as stored in memory 40.

Processor 34 may also control therapy delivery module 42 to deliver each pulse, or a burst of pulses, according to a different program of the therapy instructions, such that multiple programs of stimulation are delivered an interleaved or alternating basis. In some embodiments, processor 34 may control therapy delivery module 42 to deliver a substantially continuous stimulation waveform rather than pulsed stimulation.

In other cases, as described above, therapy delivery module 42 may include one or more fluid reservoirs and one or more pump units that pump fluid from the fluid reservoirs to the target site through the fluid delivery devices that form therapy delivery elements 44 under the control of the therapy instructions received from processor 34. For example, processor 34 may control which drugs are delivered and the dosage, rate and lockout interval of the drugs delivered. The fluid reservoirs may contain a drug or mixture of drugs. The fluid reservoirs may provide access for filling, e.g., by percutaneous injection of fluid via a self-sealing injection port. The fluid delivery devices may comprise, for example, fluid delivery conduits in the form of catheters that deliver, i.e., infuse or disperse, drugs from the fluid reservoirs to the same or different target sites.

In some cases, therapy delivery module 42 may include an audio signal generator, a visual signal, or a tactile stimulus (e.g., vibration) generator for cueing to disrupt akinesia or treat other conditions. Processor 34 may control therapy delivery module 42 to deliver audio, visual or tactile cueing with different parameters, such as amplitude, frequency, or the like, as specified by programs stored in memory 40.

Processor 34 also may control a telemetry module 38 to exchange information with an external programmer, such as a clinician programmer and/or patient programmer, by wireless, radio frequency (RF) telemetry. Processor 34 may control telemetry module 38 to communicate with the external programmer on a continuous basis, at periodic intervals, or upon request from the programmer. The programmer may, in turn, be connected to a computer that can program the device for algorithm and sensing adjustments, for issuing commands, for uplinking recorded loop data and for providing analysis. In addition, in some embodiments, telemetry module 38 may support wireless communication with one or more wireless sensors or sensing elements that sense physiological signals and transmit the signals to sensing and analysis circuitry 10 by wireless transmission.

Figure 7:
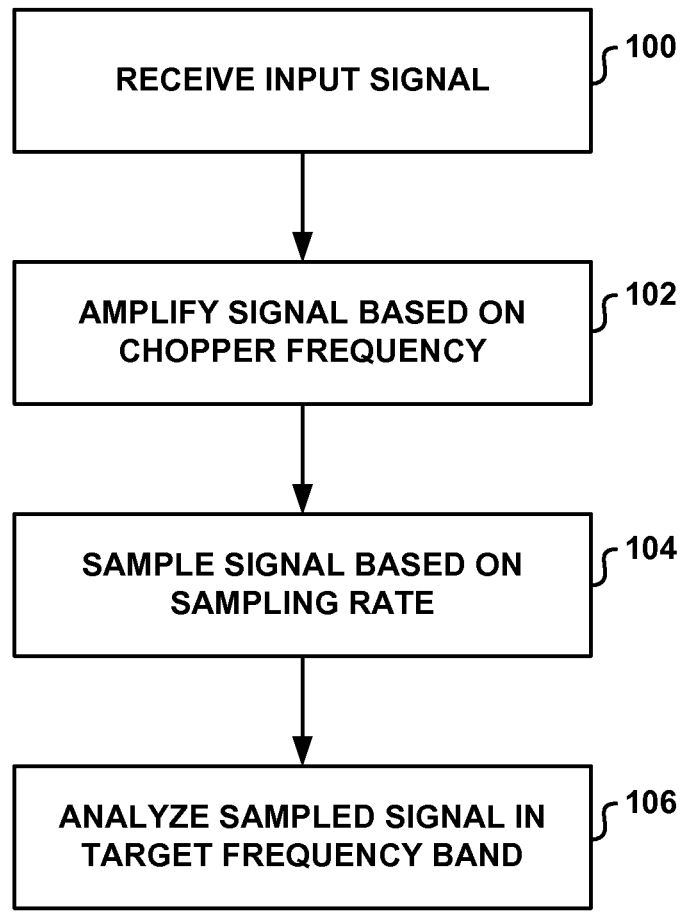
FIG. 7 is a flow diagram illustrating an example technique for controlling spectral aggressors according to this disclosure.

FIG. 7 is a flow diagram illustrating an example technique for controlling spectral aggressors according to this disclosure. Chopper amplifier 12 receives an input signal (100), and amplifies the signal based on a chopper frequency (102). For example, chopper amplifier 12 may generate a chopper-stabilized amplified version of the input signal based on the chopper frequency. ADC 14 samples the amplified signal at a sampling rate to produce a sampled signal (104). Processor 16 analyzes information contained in a target frequency band of the sampled signal (106). For example, processor 16 may determine a power magnitude or an amount or frequency of power fluctuation.

According to this disclosure, the chopper frequency and the sampling rate cause spectral interference that is generated by the chopper frequency to occur in the sampled signal at one or more frequencies that are outside of the target frequency band of the sampled signal. For example, one or more of the chopper frequency and the sampling rate may be selected and/or configured such that spectral interference caused by the chopper frequency occurs in the sampled signal at one or more frequencies that are outside of the target frequency band of the sampled signal.

Any of the chopper frequency and/or sampling rate selection and configuration techniques of this disclosure may be used to select and/or configure the chopper frequency and/or sampling rate. For example, one or more of the chopper frequency and the sampling rate may be selected and/or configured based on one or more of equations (1)-(3) and a target spectral aggressor frequency. The target spectral aggressor frequency may be selected based on the target frequency band of interest (e.g., based on one or more of an upper bound frequency and a lower bound frequency of the target frequency band of interest).

The sense electronics in a medical device (e.g., an implantable medical device) may rely on a principle known as chopper stabilization. Inputting a digital clock into analog circuitry can result in aggressors that generate unwanted noise. The techniques of this disclosure may move spectral content of the aggressor away from areas of interest by, in some examples, selecting a rate for the chopper clock.

With a clocked amplifier, such as, e.g., a chopper-stabilized amplifier, there may be a strong aggressor that shows up in the output at the clock frequency ($F_{master}$) that is used for chopper stabilization. It may be difficult to design and/or implement low-pass filters that have enough rolloff to completely eliminate the Fmaster aggressor when the amplifier is sensing 1 uV signals. When the chopper amplifier output is then sampled at a clock frequency, Fs, the aggressor tone may shift to Fs/2±delta (see, e.g., FIG. 3C). In this case, delta may represent the difference between Fmaster and n*Fs+Fs/2 for a sampled data system with an aggressor. If the delta is large, the aggressor tone may fold into the signal band of interest.

In some examples, the techniques of this disclosure may set Fmaster (i.e., the chopper clock)=n*Fs+(Fs/2) and set Fs (i.e., the sampling rate)=4×BW (i.e., the bandwidth of the input signal) so the aggressor lands at 2 times the bandwidth of the input signal and out of band of interest set at BW. In some cases, the bandwidth of the input signal may be equal to the maximum frequency of the input signal. In other words, the bandwidth of the input signal, in such cases, may be equal to the difference between the upper bound frequency of the input signal and 0 Hz (i.e., a DC frequency). In further examples, the techniques of this disclosure may change the rate of in-system digital signals, such as, e.g., the chopper clock to move spectral aggressors out of a target frequency band of interest.

The techniques of this disclosure may be used to move spectral aggressors that are caused by a chopper frequency to a portion of the sampled signal that is outside of the target frequency band of interest, which may reduce the amount of noise in the target frequency band of the sampled signal. In this manner, a signal monitoring device may be able to monitor characteristics of the target frequency band without interference from and/or with reduced interference from chopper frequency spectral aggressors.

Various techniques described in this disclosure may be implemented in hardware, software, firmware or any combination thereof. For example, various aspects of the techniques may be implemented within or in conjunction with one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to cause a processor to perform or support one or more aspects of the functionality described in this disclosure.

Various aspects and examples have been described. However, modifications can be made to the structure or techniques of this disclosure without departing from the scope of the following claims.

The invention claimed is:

1. A signal monitoring device comprising:
   a chopper amplifier configured to receive an input signal and generate a chopper-stabilized amplified version of the input signal based on a chopper frequency;
   an analog-to-digital converter configured to sample the chopper-stabilized amplified version of the input signal at a sampling rate to generate a sampled signal; and
   a processor configured to analyze a target frequency band of the sampled signal,
   wherein the chopper frequency and the sampling rate cause spectral interference that is generated by the chopper frequency to occur in the sampled signal at one or more frequencies that are outside of the target frequency band of the sampled signal, and
   wherein the chopper frequency is equal to one of:
      an odd multiple of one half of the sampling rate, or
      an odd multiple of one half of the sampling rate plus or minus a difference between one half of the sampling rate and a target spectral aggressor frequency that is outside of the target frequency band of the sampled signal.

2. The device of claim 1, wherein the chopper frequency is greater than a 1/f corner frequency of an amplifier included in the chopper amplifier.

3. The device of claim 1, wherein the chopper frequency is configured to satisfy the following equation:

$$F_{master} = n * F_S + F_S/2$$

where $F_{master}$ is the chopper frequency, $F_S$ is the sampling rate, and n is a non-negative integer.

4. The device of claim 3, wherein n is selected based on at least one of a noise characteristic of an amplifier included in the chopper amplifier, a flicker noise characteristic of the amplifier included in the chopper amplifier, and a 1/f corner frequency of the flicker noise characteristic of the amplifier included in the chopper amplifier.

5. The device of claim 3, wherein n is selected such that the chopper frequency is greater than a 1/f corner frequency of an amplifier included in the chopper amplifier.

6. The device of claim 1, wherein the chopper frequency is configured to satisfy the following equations:

$$\delta = \frac{F_S}{2} - F_{target}$$

$$F_{master} = n * F_S + \frac{F_S}{2} \pm \delta$$

where $F_{master}$ is the chopper frequency, $F_{target}$ is a target spectral aggressor frequency, $F_S$ is the sampling rate, and n is a non-negative integer.

7. The device of claim 6, wherein n is selected based on at least one of a noise characteristic of an amplifier included in the chopper amplifier, a flicker noise characteristic of the amplifier included in the chopper amplifier, and a 1/f corner frequency of the flicker noise characteristic of the amplifier included in the chopper amplifier.

8. The device of claim 6, wherein n is selected such that the chopper frequency is greater than a 1/f corner frequency of an amplifier included in the chopper amplifier.

9. The device of claim 1, wherein the input signal is a brain signal and the target frequency band is one of an alpha, beta, gamma or fast ripple frequency band of the brain signal.

10. The device of claim 9, wherein the brain signal comprises at least one of an electroencephalogram (EEG) signal, an electrocorticogram (ECoG) signal, a local field potential (LFP) signal, or a single cell action potential signal.

11. The device of claim 1, wherein the processor is further configured to determine a power level of the target frequency band in the sampled signal.

12. The device of claim 1, wherein the processor is further configured to determine a power fluctuation of the target frequency band in the sampled signal.

13. The device of claim 1, wherein the chopper amplifier is further configured to:
   modulate an amplitude of the input signal based on the chopper frequency to produce a modulated signal;
   amplify an amplitude of the modulated signal to produce an amplified signal;
   demodulate the amplified signal to produce a demodulated signal; and
   generate the chopper-stabilized amplified version of the input signal based on the demodulated signal.

14. The device of claim 13, wherein the chopper amplifier is further configured to low-pass filter the demodulated signal to generate the chopper-stabilized amplified version of the input signal.

15. The device of claim 1, wherein the chopper amplifier, the analog-to-digital converter, and the processor are included in an implantable medical device.

16. A method for monitoring a signal comprising:
   generating a chopper-stabilized amplified version of an input signal based on a chopper frequency;
   sampling the chopper-stabilized amplified version of the input signal at a sampling rate to generate a sampled signal; and
   analyzing information contained in a target frequency band of the sampled signal,
   wherein the chopper frequency and the sampling rate cause spectral interference that is generated due to the chopper frequency to occur in the sampled signal at a frequency that is outside of the target frequency band of the sampled signal, and
   wherein the chopper frequency is equal to one of:
      an odd multiple of one half of the sampling rate, or
      an odd multiple of one half of the sampling rate plus or minus a difference between one half of the sampling rate and a target spectral aggressor frequency that is outside of the target frequency band of the sampled signal.

17. The method of claim 16, wherein the chopper frequency is greater than a 1/f corner frequency of an amplifier included in the chopper amplifier.

18. The method of claim 16, wherein the chopper frequency is configured to satisfy the following equation:

$$F_{master} = n*F_S + F_S/2$$

where $F_{master}$ is the chopper frequency, $F_S$ is the sampling rate, and n is a non-negative integer.

19. The method of claim 18, wherein n is selected based on at least one of a noise characteristic of an amplifier included in the chopper amplifier, a flicker noise characteristic of the amplifier included in the chopper amplifier, and a 1/f corner frequency of the flicker noise characteristic of the amplifier included in the chopper amplifier.

20. The method of claim 18, wherein n is selected such that the chopper frequency is greater than a 1/f corner frequency of an amplifier included in the chopper amplifier.

21. The method of claim 16, wherein the chopper frequency is configured to satisfy the following equations:

$$\delta = \frac{F_S}{2} - F_{target}$$

$$F_{master} = n*F_S + \frac{F_S}{2} \pm \delta$$

where $F_{master}$ is the chopper frequency, $F_{target}$ is a target spectral aggressor frequency, $F_S$ is the sampling rate, and n is a non-negative integer.

22. The method of claim 21, wherein n is selected based on at least one of a noise characteristic of an amplifier included in the chopper amplifier, a flicker noise characteristic of the amplifier included in the chopper amplifier, and a 1/f corner frequency of the flicker noise characteristic of the amplifier included in the chopper amplifier.

23. The method of claim 21, wherein n is selected such that the chopper frequency is greater than a 1/f corner frequency of an amplifier included in the chopper amplifier.

24. The method of claim 16, wherein the input signal is a brain signal and the target frequency band is one of an alpha, beta, gamma or fast ripple frequency band of the brain signal.

25. The method of claim 24, wherein the brain signal comprises at least one of an electroencephalogram (EEG) signal, an electrocorticogram (ECoG) signal, a local field potential (LFP) signal, or a single cell action potential signal.

26. The method of claim 16, further comprising determining a power level of the target frequency band in the sampled signal.

27. The method of claim 16, further comprising determining a power fluctuation of the target frequency band in the sampled signal.

28. The method of claim 16, wherein generating the chopper-stabilized amplified version of the input signal based on the chopper frequency comprises:
modulating an amplitude of the input signal based on the chopper frequency to produce a modulated signal;
amplifying an amplitude of the modulated signal to produce an amplified signal;
demodulating the amplified signal to produce a demodulated signal; and
generating the chopper-stabilized amplified version of the input signal based on the demodulated signal.

29. The method of claim 28, wherein generating the chopper-stabilized amplified version of the input signal based on the demodulated signal comprises low-pass filtering the demodulated signal to generate the chopper-stabilized amplified version of the input signal.

30. The method of claim 16,
wherein generating the chopper-stabilized amplified version of the input signal comprises generating, with a chopper amplifier, the chopper-stabilized amplified version of the input signal,
wherein sampling the chopper-stabilized amplified version of the input signal comprises sampling, with an analog-to-digital converter, the chopper-stabilized amplified version of the input signal,
wherein analyzing the information comprises analyzing, with a processor, the information, and
wherein the chopper amplifier, the analog-to-digital converter, and the processor are included in an implantable medical device.

31. An apparatus comprising:
means for generating a chopper-stabilized amplified version of an input signal based on a chopper frequency;
means for sampling the chopper-stabilized amplified version of the input signal at a sampling rate to generate a sampled signal; and
means for analyzing information contained in a target frequency band of the sampled signal,
wherein the chopper frequency and the sampling rate cause spectral interference that is generated due to the chopper frequency to occur in the sampled signal at a frequency that is outside of the target frequency band of the sampled signal, and
wherein the chopper frequency is equal to one of:
an odd multiple of one half of the sampling rate, or
an odd multiple of one half of the sampling rate plus or minus a difference between one half of the sampling rate and a target spectral aggressor frequency that is outside of the target frequency band of the sampled signal.

32. An implantable medical device (IMD) comprising:
stimulation circuitry;
sensing and analysis circuitry comprising:
a chopper amplifier configured to receive an input signal and generate a chopper-stabilized amplified version of the input signal based on a chopper frequency; and
an analog-to-digital converter configured to sample the chopper-stabilized amplified version of the input signal at a sampling rate to generate a sampled signal,
wherein the chopper frequency and the sampling rate cause spectral interference that is generated by the chopper frequency to occur in the sampled signal at one or more frequencies that are outside of a target frequency band of the sampled signal, and
wherein the chopper frequency is equal to one of:
an odd multiple of one half of the sampling rate, or
an odd multiple of one half of the sampling rate plus or minus a difference between one half of the sampling rate and a target spectral aggressor frequency that is outside of the target frequency band of the sampled signal; and
a processor configured to analyze the target frequency band of the sampled signal, and control the stimulation circuitry to deliver therapy based on the analysis of the target frequency band.

33. The IMD of claim 32, wherein the chopper frequency is configured to satisfy the following equation:

$$F_{master} = n*F_S + F_S/2$$

where $F_{master}$ is the chopper frequency, $F_S$ is the sampling rate, and n is a non-negative integer based on at least one of a noise characteristic of an amplifier included in the chopper amplifier, a flicker noise characteristic of the amplifier included in the chopper amplifier, and a 1/f corner frequency of the flicker noise characteristic of the amplifier included in the chopper amplifier.

34. The IMD of claim 32, wherein the chopper frequency is configured to satisfy the following equations:

$$\delta = \frac{F_S}{2} - F_{target}$$

$$F_{master} = n * F_S + \frac{F_S}{2} \pm \delta$$

where $F_{master}$ is the chopper frequency, $F_{target}$ is a target spectral aggressor frequency, $F_S$ is the sampling rate, and n is a non-negative integer based on at least one of a noise characteristic of an amplifier included in the chopper amplifier, a flicker noise characteristic of the amplifier included in the chopper amplifier, and a 1/f corner frequency of the flicker noise characteristic of the amplifier included in the chopper amplifier.

* * * * *